United States Patent
Singfield

(10) Patent No.: US 9,291,486 B2
(45) Date of Patent: Mar. 22, 2016

(54) METHOD AND SYSTEM FOR MEASURING FLUID FLOW IN BELL NIPPLES USING PRESSURE MEASUREMENT

(75) Inventor: Christian Robert Maurice Singfield, Auchenflower (AU)

(73) Assignee: MEZURX PTY LTD, Auchenflower (AU)

( * ) Notice: Subject to any disclaimer, the term of this patent is extended or adjusted under 35 U.S.C. 154(b) by 186 days.

(21) Appl. No.: 13/989,328

(22) PCT Filed: Nov. 8, 2011

(86) PCT No.: PCT/AU2011/001423
§ 371 (c)(1),
(2), (4) Date: Jul. 29, 2013

(87) PCT Pub. No.: WO2012/068610
PCT Pub. Date: May 31, 2012

(65) Prior Publication Data
US 2013/0298696 A1    Nov. 14, 2013

(30) Foreign Application Priority Data

Nov. 24, 2010 (AU) ............................... 2010905207
Jun. 6, 2011 (AU) ............................... 2011902220

(51) Int. Cl.
| | | |
|---|---|---|
| G01F 1/34 | (2006.01) | |
| E21B 21/08 | (2006.01) | |
| G01N 9/26 | (2006.01) | |
| G01F 1/36 | (2006.01) | |
| G01F 1/50 | (2006.01) | |
| G01F 1/84 | (2006.01) | |
| G01F 1/88 | (2006.01) | |

(52) U.S. Cl.
CPC . *G01F 1/34* (2013.01); *E21B 21/08* (2013.01); *G01F 1/36* (2013.01); *G01F 1/50* (2013.01); *G01F 1/84* (2013.01); *G01F 1/88* (2013.01); *G01N 9/26* (2013.01)

(58) Field of Classification Search
None
See application file for complete search history.

(56) References Cited

U.S. PATENT DOCUMENTS

| | | | |
|---|---|---|---|
| 3,827,295 A | | 8/1974 | Rochon et al. |
| 4,408,486 A | | 10/1983 | Rochon et al. |
| 2002/0184940 A1 | * | 12/2002 | Storm et al. ................. 73/32 A |
| 2004/0249583 A1 | | 12/2004 | Eryurek et al. |
| 2008/0053242 A1 | * | 3/2008 | Schumacher .............. 73/861.42 |
| 2008/0306892 A1 | | 12/2008 | Crossley et al. |
| 2013/0291620 A1 | * | 11/2013 | Singfield ....................... 73/1.35 |
| 2013/0298663 A1 | * | 11/2013 | Singfield ................... 73/152.34 |

OTHER PUBLICATIONS

International Search Report for PCT/AU2011/001423, dated Jan. 31, 2012 (3 pages).

* cited by examiner

*Primary Examiner* — Harshad R Patel
(74) *Attorney, Agent, or Firm* — K&L Gates LLP

(57) ABSTRACT

The volumetric rate of flow out of a flow line (4) of a bell nipple (2) is a function of the pressure of the head of liquid (7) above the threshold of the intersection of the vertical pipe (3) and the flow line (4). A pressure which is related to that pressure is measured by a pressure transducer (10) which is mounted below the threshold. Density of the fluid (7) is inferred by using the measured pressure as an input to a trained neural network.

4 Claims, 2 Drawing Sheets

METHOD AND SYSTEM FOR MEASURING FLUID FLOW IN BELL NIPPLES USING PRESSURE MEASUREMENT

FIELD OF THE INVENTION

The present application is the national stage of PCT/AU2011/001423, filed on Nov. 8, 2011, which is incorporated herein by reference and which claims the benefit under 35 U.S.C. §§119(a) and 365(b) of Australian Patent Application Serial No. 2010905207, filed on Nov. 24, 2010 and of Australian Patent Application Serial No. 2011 902220, filed on Jun. 6, 2011, both of which are incorporated herein by reference in their entireties.

BACKGROUND OF THE INVENTION

Drilling muds are usually water-based, but they can be based on other liquids such as synthetic oils. Additives are mixed with the liquid base. Common additives to water-based drilling muds include solids such as barite, chalk (calcium carbonate) and haematite. It is required that these added solids be homogeneously mixed with the liquid base, and that the homogeneity be maintained.

The physical and chemical characteristics of drilling mud also varies during the process of drilling. Depending on the geology at the depth of the drill bit, it may be necessary for the driller to actively vary any one or more of the density, viscosity, pH, or other chemical or physical property of the drilling mud. In the oil industry, when drilling a borehole, the drilling muds used during the life-cycle of a single borehole could begin with water, then move to a water based mud, then move from the water-based mud to a synthetic oil based mud. These drilling muds have a complex range of physical characteristics and the characteristics required at any particular stage of the drilling process vary during the drilling life-cycle. Physical or chemical characteristics of the mud may also vary depending on events which are not under the control of the driller. The invasion of petroleum products into the bore hole is such an event, and will cause a "kick" or impulse change in the characteristics of the drilling mud, causing sudden variations in, for example, the density and/or viscosity of the mud.

It is accordingly important for the driller to monitor volumetric flows of the drilling mud.

SUMMARY OF THE INVENTION

Accordingly, in one aspect, embodiments of the present invention provide a method of
 measuring the flow rate of a liquid over a threshold, comprising:
 determining a pressure which is related to the pressure of the head of liquid above the threshold; and
 using the determined pressure to infer the flow rate of the liquid over the threshold.
In various embodiments, the determined pressure is used as an input to a trained neural network to infer the flow rate of liquid over the threshold.
In various embodiments, the mass flow rate of the liquid over the threshold is derived by multiplying the volume flow rate over that threshold by the density of the liquid.
In various embodiments, the density of the liquid is derived by a process which comprises measuring the difference in pressure of the fluid between two vertically spaced levels.
In various embodiments, the pressure which is related to the pressure of the head of liquid above the threshold is determined by measuring a height which is related to the pressure of the head of liquid above the threshold.

In another aspect, embodiments of the invention provide apparatus for measuring the volume flow rate of a flow of liquid over a threshold.

BRIEF DESCRIPTION OF THE DRAWINGS

So that the present invention may be more readily understood, preferred embodiments of it are described in conjunction with the accompanying drawings in which.

DESCRIPTION OF PREFERRED EMBODIMENTS OF THE INVENTION

Structure

Figure 1:
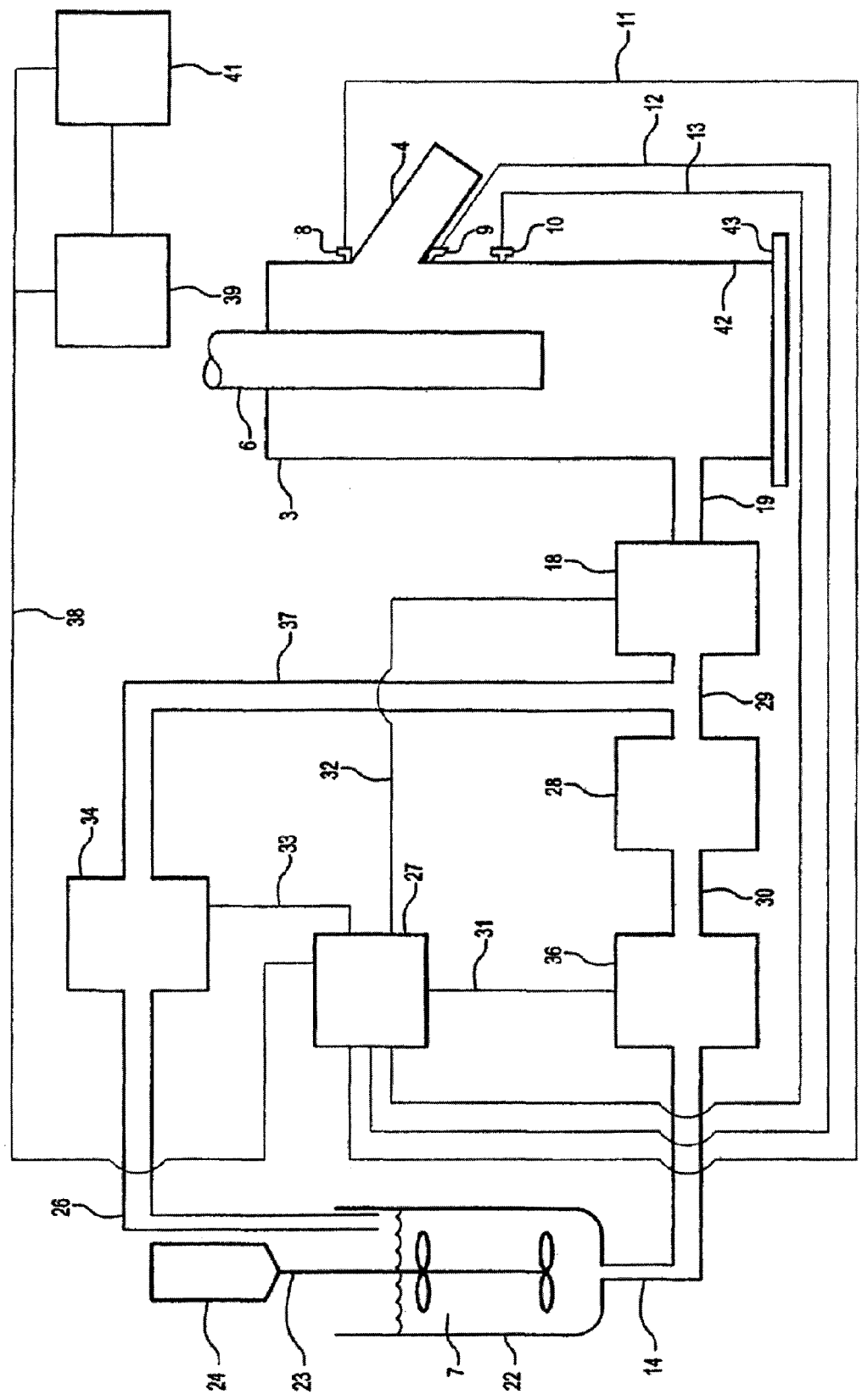
FIG. 1 is a fragmentary illustration of a portion of a drilling rig, partly schematic and partially in cross-section, according to preferred embodiments of the present invention.
Figure 2:
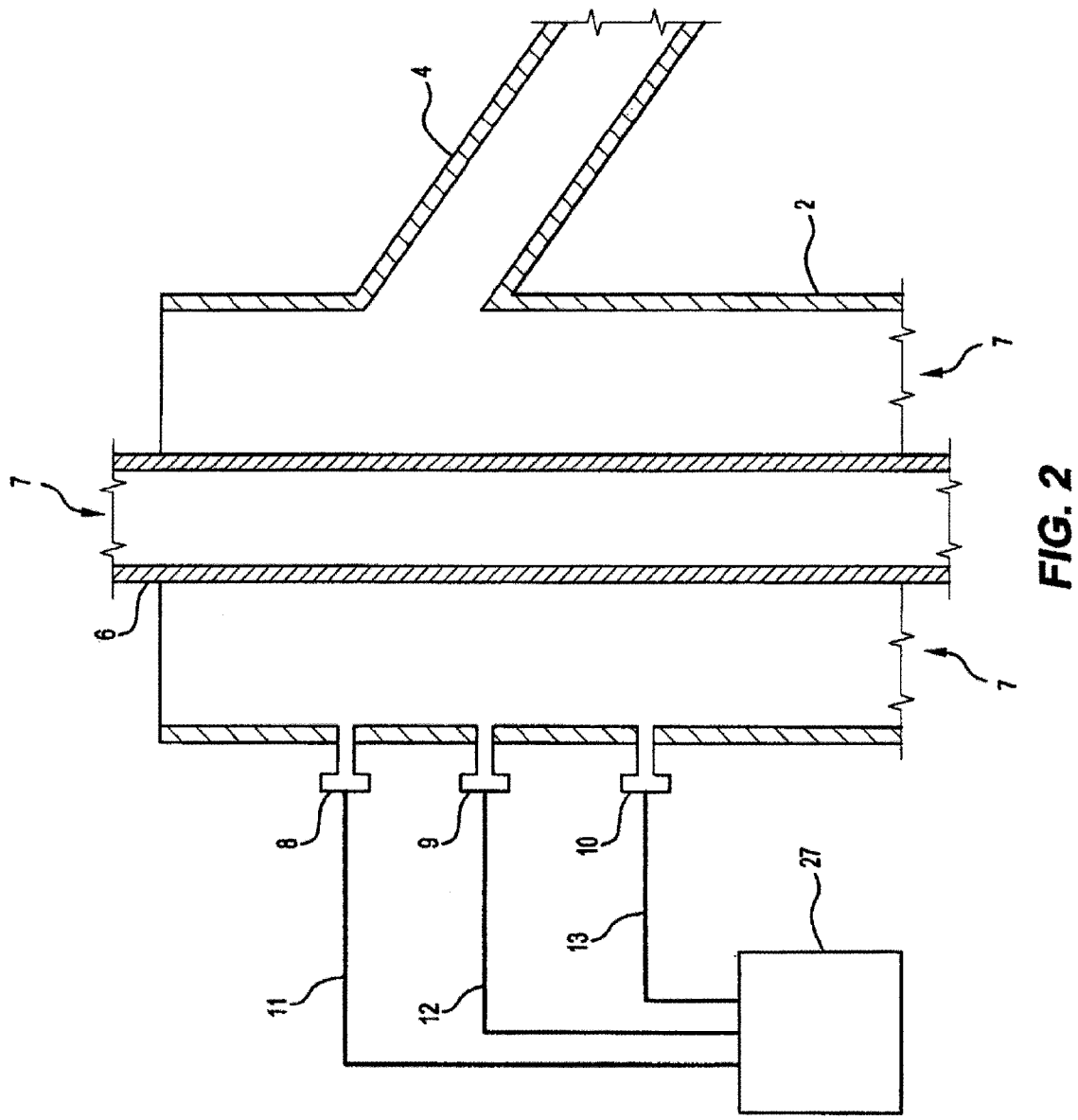
FIG. 2 is an illustration of apparatus, partly schematic and partially in cross-section, according to preferred embodiments of the present invention.

As is illustrated in FIGS. 1 and 2, a conventional drilling rig comprises a bell nipple 2. The bell nipple 2 comprises a large diameter pipe 3 which has a flow line 4 protruding 5 from it. In use a bell nipple 2 is fitted to the top of the blowout preventers (which are not shown in the drawings) when drilling an oil or gas bore. Drill steel 6 passes coaxially through the bell nipple 2. During drilling, drilling mud 7 is pumped down into the drill bole through the drill steel 6 and returns to the surface. When the drilling mud 7 enters the bell nipple 2, that mud 7 flows through the annular cavity between the outer periphery of the drill steel 6 and the inner wall of the pipe 3 until it reaches the intersection between the pipe 3 and the flow line 4. The drilling mud 7 then flows out of the flow line 4.

According to preferred embodiments of the present invention, a pressure transducer 10 is mounted to the pipe 3 at a vertical level which is a known distance below the lowermost point of intersection between the pipe 3 and the flow line 4. The pressure transducer 10 measures the pressure of the drilling mud which is within the large diameter pipe 3 of the bell nipple 2. A signal line 13 interconnects the pressure transducer 10 and the digital processor 27.

According to alternative preferred embodiments of the present invention, further pressure transducers are mounted to the pipe 3 at known vertically-spaced positions. FIGS. 1 and 2 accordingly illustrate further pressure transducers;
 a top pressure transducer 8 which is interconnected by a signal line 11 to the digital processor 27; and
 a middle pressure transducer 9 which is interconnected by a signal line 12 to the digital processor 27.

FIG. 2 illustrates the apparatus of FIG. 1 in the context of a mud supply system according to embodiments of the present invention. As is described below under the heading of "Operation", the configuration of apparatus which is illustrated in FIG. 1 illustrates apparatus as it is configured for the purposes of calibration.

In the embodiment of the invention that is illustrated in FIG. 1, a tank 22 for the supply of drilling mud 7 or the like is connected by pipe 14 to the input side of a pressure differential flow meter 36.

The output side of the pressure differential flow meter 36 is in turn connected through pipe 30 to the input of a charge pump 28. The preferred form of pump for the charge pump 28 is a centrifugal pump.

The output of the charge pump 28 is connected through a T-junction comprising pipes 29 and 37 to a positive displacement pump 18 and to a Coriolis meter 34 respectively. The preferred form of positive displacement pump is a piston pump. The Coriolis meter 34 is a type of meter that can be used to measure all of the density, the mass flow rate and the volumetric flow rate of liquid that is flowing through it. However, a Coriolis meter is not suitable for measuring the very high flows that are involved in the supply of drilling mud 7 to a drill hole.

The output of the positive displacement pump 18 is connected to pipe 19 for purposes which are described below. The output of the Coriolis meter 34 is connected to pipe 26 which connects as an input to the mud tank 22. A mixer 23 is mounted within the tank 22 and is driven by an electric motor 24.

Data and control lines 31, 32 and 33 interconnect a digital processor 27 with the pressure differential meter 36, the positive displacement pump 18 and the Coriolis meter 34 respectively. For purposes which are described below, control signals over the lines 31 and 33 between the processor 17 and the meters 13 and 14 are according to the "HART Field Communication Protocol Specifications" which are available from HART Communication Foundation, 9390 Research Boulevard, Suite 1-350, Austin, Tex., USA.

According to a particularly preferred embodiment, the digital processor 27 is an Allen-Bradley CompactLogiX programmable logic controller (PLC). The digital processor 27 is connected to the Ethernet network 38.

A plant historian server 39 is also connected to the Ethernet network 38. According to a particularly preferred embodiment of the invention, the plant historian server 39 runs the Wonderware InSQL software supplied by Wonderware of 26561 Rancho Parkway, South Lake Forest, Calif., USA. This plant historian is used to collect plant data preferably at a 500 msec sampling rate.

A soft-sensor server 41 is also connected to the Ethernet network 38. The approach to measuring a process variable where no instrument is available to directly measure that variable is termed a soft-sensor. A soft-sensor is simply a calculation which extracts signal from available measurements in a high noise non-linear environment. The soft-sensor is therefore said to produce an inferred or soft measurement. The neural network used in the presently-described embodiments of the invention has a feedforward structure, two hidden layers, a sigmoid type transfer function and is trained using a modified backpropagation algorithm. An error backpropagation algorithm was used for training. This is a common type of neural network paradigm and is described in Lipták, B. G., (editor); *Process Control, Instrument Engineers Handbook 3rd edition, Section* 1.7, *Expert Systems—Neural Networks*, by B. A. Jensen (1994), Chilton Book Company, Radnor, Pa. (1995). As is described in more detail below, inputs to the neural network include three pressure measurements (from the pressure transducers 8, 9 and 10) and the drill pipe rotary speed.

Operation—Mud Supply

The embodiment of the invention that is illustrated in FIGS. 1 and 2 utilizes a supply of drilling mud 7 in surface tanks 22. The mud 7 in the tank 22 is kept in a relatively homogeneous state using the mixer 23 which is driven by the electric motor 24. Operation of the charge pump 28 draws mud 7 off from tank 22 through pipe 14, through the pressure differential meter 36, through the charge pump 28, to the T-junction comprised by pipes 29 and 37. In flowing through the pressure differential meter 36, the mud 7 generates a pressure differential which is monitored by the digital processor 27.

The largest portion of the flow out of the charge pump 28 flows through pipe 29 into the input of the positive displacement pump 18 and from the output of the positive displacement pump into the bore hole (which is not illustrated in the drawings). A small portion of the flow out of the charge pump 28 flows through pipe 37 to the input of the Coriolis meter 34 and from the output of the Coriolis meter 34 through the pipe 26 back to the tank 22.

A pressure differential meter (or Venturi) meter relies on Bernoulli's equation, namely:

$$p + \rho g h + \tfrac{1}{2}\rho v^2 = \text{a constant}$$

where
 "p" is the pressure of a liquid;
 "ρ" is the density of the liquid;
 "g" is the acceleration due to gravity;
 "h" is the height of the liquid; and
 "v" is the velocity of the liquid.

However, as explained above, in the case of drilling mud the density "ρ" of the liquid varies and so it is necessary to know the (variable) density of the mud 6 that is flowing through the Venturi meter 36 in order to calculate the volumetric flow of mud 7 through that meter.

The Coriolis meter 34 accordingly takes a small proportion of the total flow of drilling mud 7 from the outlet of the charge pump 28 and measures the density and flow-rate of that small flow. The density of the mud 7 as measured by the Coriolis meter 34 is used, together with pressure differential across the wedge as measured in the Venturi meter 36, to calculate either or both of the mass flow rate and the density flow rate through the Venturi meter 36. According to some preferred embodiments of the invention, these calculations are performed by the digital processor 27. The digital processor 27 also compensates for differences in the times taken for mud 7 to flow from the tank 22 to each of:
 the Venturi meter 36;
 the positive displacement pump 28; and
 the Coriolis meter 34.

The flow rate through the positive displacement pump 18 is equal to the calculated flow rate through the Venturi meter 36 minus the measured flow rate through the Coriolis meter 34. The digital processor 27 also calculates this flow rate.

The digital processor 27 also monitors the volumetric flow rate through the positive displacement pump 18 as calculated from counted pump strokes. This flow rate as measured by counting pump strokes should be the same as the calculated flow rate through the positive displacement pump 18. However, differences in:
 flow as calculated by counting pump strokes; and
 flow as calculated by the difference between flow through the Venturi meter and
 flow through the Coriolis meter,
may indicate that maintenance is due on one or more of those meters. In particular, variations in these differences which show that the flow as calculated by measuring pump strokes is greater than the calculated flow through the positive displacement pump 18 is an indicator that the positive displacement pump 8 may be due for maintenance.

According to other preferred embodiments of the invention which are not illustrated in the drawings, mud density as measured by the Coriolis meter 34 are passed directly to electronic circuitry that is associated with the Venturi meter 36.

The processor 27 monitors the density of the mud 7 to determine whether or not that density is reaching the range limit of the pressure differential meter 36 or the Coriolis meter 34. When the density reaches that limit, the processor uses the HART protocol to take the relevant meter 36 or 34 offline. The processor 27 suppresses any alarm which would show that the meter is offline or stopped and uploads new calibration data to that instrument. This new calibration data allows the instrument to handle a different density range. The processor 27 then puts the meter 36 or 34 back online.

Operation—Calibration of the Bell Nipple

Before use of the bell nipple 2 in the field, a calibration exercise is performed on it. For this calibration, the lower end 42 of the bell nipple 2 is blanked-off such as by use of a removable plate 43. During drilling operations mud flow would flow from the positive displacement pump 18 into the drill steel 6, out of the drill bit at the bottom of the bore hole, and back up from the drill hole to the bell nipple 2 and out the flow line 4. However during the calibration exercises liquid 7 is pumped into the lower portion of the bell nipple 2 below the lowest pressure transducer 10.

The calibration exercise comprises pumping a liquid 7 upwards through the bell nipple 2 while monitoring the pressure of the head of that fluid above the pressure transducer 10. For the purposes of the calibration, the relevant physical properties of the liquid (such as temperature, density and viscosity) are known. The drill steel 6 is also driven at a range of rotational speeds which are expected during actual operation of the drilling rig.

Multiple calibration runs are performed using liquids of different density. For each density of liquid the flow rate of liquid 7 is varied from the minimum expected flow rate to the maximum expected flow rate, and the pressure as measured by the lowest pressure transducer 10 is monitored. As liquid 7 is pumped into the bell nipple 2, the level of that fluid within the bell nipple will rise until it reaches the threshold of the intersection of the pipe 3 and the flow line 4 at which time the middle pressure transducer 9 will register a pressure. Depending on the rate at which the liquid 1 is being pumped into the bell nipple 2, the level of liquid 7 will then rise further and may rise above the upper level of the intersection of the pipe 3 and the flow line 4. When the liquid 7 rises above that point, the uppermost and the pressure transducer 8 will register a pressure measurement.

Example 1

Calibration runs were performed using water and using drilling muds with which densities which ranged from 9 to 19 pounds per gallon. The neural network soft sensor was trained with the data on the pressure measured by the transducer 10 which was acquired during these calibration runs. In each case, the neural network soft sensor has a measured accuracy against a 6 inch Coriolis flowmeter of ±0.31%

According to alternative preferred embodiments of the invention which are not illustrated in the drawings, the determination of a pressure which is related to the pressure of the head of liquid above the threshold is not achieved by the user of pressure transducers. Instead, sensors are used to determine the height of the fluid at some point upstream of the threshold and from this height measurement a pressure is inferred.

In order to ascertain the mass flow rate of liquid out of the flow line 4, preferred embodiments of the invention utilize pressure measurements taken by the middle pressure transducer 9. As the vertical distance between the lower pressure transducer 10 and the middle pressure transducer 9 is known, the difference in pressure measurements between these two transducers is used to calculate the density of the fluid 7. The mass flow rate of the fluid 7 is then the product of the density of that fluid and its volumetric flow rate.

Various embodiments of the invention may be embodied in many different forms, including computer program logic for use with a processor (eg., a microprocessor, microcontroller, digital signal processor, or general purpose computer), programmable logic for use with a programmable logic device (eg, a field programmable gate array (FPGA) or other PLD), discrete components, integrated circuitry (eg., an application specific integrated circuit (ASIC)), or any other means including any combination thereof. In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, Ruby, or HTML) for use with various operating systems or operating environments. The source code may define and use various data structures and communication messages. The source code may be in a computer executable form (e.g., via an interpreter), or the source code may be converted (e.g., via a translator, assembler, or compiler) into computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the internet or world wide web).

Hardware logic (including programmable logic for use with a programmable logic device) implementing all or part of the functionality where described herein may be designed using traditional manual methods, or may be designed, captured, simulated, or documented electronically using various tools, such as computer aided design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the internet or world wide web).

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

Throughout this specification, the words "comprise", "comprising", and "comprises" are to be taken to specify the presence of stated features, integers, steps or components but does not preclude the presence or addition of one or more other features, integers, steps, components or groups thereof.

In the claims, each dependent claim is to be read as being within the scope of its parent claim or claims, in the sense that a dependent claim is not to be interpreted as infringed unless its parent claims are also infringed.

The invention claimed is:

1. A method, comprising:
deriving calibration data representing relationships between heights and densities of fluids within a bell nipple, and flow rates of the fluids through a flow line branched off the bell nipple;
measuring pressures of a fluid within the bell nipple with at least two pressure transducers vertically spaced apart along the bell nipple horizontally adjacent to the flow line;
calculating height and density of the fluid within the bell nipple based on the measured pressures; and
calculating volumetric flow rate and mass flow rate of the fluid through the flow line based on the calibration data and the calculated height and density.

2. The method of claim 1, wherein the fluid is drilling mud.

3. A system, comprising:
at least two pressure transducers vertically spaced apart along a bell nipple horizontally adjacent to a flow line branched off the bell nipple;
data storage storing calibration data representing relationships between heights and densities of fluids in the bell nipple, and flow rates of the fluids through the flow line; and
a processor in communication with the at least two pressure transducers and the data storage, wherein the processor is programmed to calculate:
height and density of a fluid within the bell nipple based on measured pressures with the at least two pressure transducers; and
volumetric flow rate and mass flow rate of the fluid through the flow line based on the calibration data and the calculated height and density.

4. The system of claim 3, wherein the fluid is drilling mud.

* * * * *